United States Patent
Chen et al.

(10) Patent No.: US 9,140,671 B2
(45) Date of Patent: Sep. 22, 2015

(54) QUANTITATIVE SENSOR AND MANUFACTURING METHOD THEREOF

(75) Inventors: Ying-Chung Chen, Kaohsiung (TW);
Chien-Chuan Cheng, Kaohsiung (TW);
Wei-Tsai Chang, Kaohsiung (TW);
Kuo-Sheng Kao, Kaohsiung (TW);
Re-Ching Lin, Kaohsiung (TW);
Jia-Ming Jiang, Kaohsiung (TW);
Chun-Hung Yang, Kaohsiung (TW)

(73) Assignee: National Sun Yat-Sen University

( * ) Notice: Subject to any disclaimer, the term of this patent is extended or adjusted under 35 U.S.C. 154(b) by 129 days.

(21) Appl. No.: 13/536,091

(22) Filed: Jun. 28, 2012

(65) Prior Publication Data

US 2013/0004370 A1    Jan. 3, 2013

(30) Foreign Application Priority Data

Jun. 28, 2011    (CN) .................. 2011 2 0222595 U
Jun. 28, 2011    (CN) .................. 2011 2 0222597 U

(51) Int. Cl.
*G01N 27/00*    (2006.01)
*G01N 29/24*    (2006.01)
*G01N 29/02*    (2006.01)

(52) U.S. Cl.
CPC .......... *G01N 29/2462* (2013.01); *G01N 29/022* (2013.01); *G01N 2291/0426* (2013.01)

(58) Field of Classification Search
CPC ............ G01N 29/2462; G01N 29/022; G01N 2291/0426
USPC ............... 422/82.01, 82.02, 98; 438/1, 48, 49
See application file for complete search history.

(56) References Cited

U.S. PATENT DOCUMENTS

| | | | |
|---|---|---|---|
| 2006/0137453 A1 | 6/2006 | Wu et al. | |
| 2006/0191320 A1* | 8/2006 | Pinnaduwage et al. | ...... 73/24.06 |
| 2006/0222568 A1* | 10/2006 | Wang et al. | ...... 422/70 |
| 2007/0000305 A1 | 1/2007 | Ma et al. | |
| 2010/0001740 A1 | 1/2010 | Rantala | |
| 2010/0282005 A1 | 11/2010 | Kwon | |

OTHER PUBLICATIONS

Qin, Lifeng, et al. "Analytical study of dual-mode thin film bulk acoustic resonators (FBARs) based on ZnO and AlN films with tilted c-axis orientation." Ultrasonics, Ferroelectrics and Frequency Control, IEEE Transactions on 57.8 (2010): 1840-1853.*

Ito, Yukio, et al. "A 100-MHz ultrasonic transducer array using ZnO thin films."Ultrasonics, Ferroelectrics and Frequency Control, IEEE Transactions on 42.2 (1995): 316-324.*

* cited by examiner

*Primary Examiner* — Paul Hyun
*Assistant Examiner* — Robert Eom
(74) *Attorney, Agent, or Firm* — Muncy, Geissler, Olds & Lowe, P.C.

(57) ABSTRACT

A quantitative sensor and manufacture method thereof are disclosed. This quantitative sensor has a dual-mode film bulk acoustic resonator structure to achieve desirable performances in sensitivity, accuracy and efficiency. Furthermore, this quantitative sensor serves as a fluid sensor when a fluid detection metal layer is formed in a sample-receiving chamber; and this quantitative sensor may also serve as a bio sensor when biocompatible metal layer and a bio-sensing layer are formed in the sample-receiving chamber instead of the fluid detection metal layer.

14 Claims, 5 Drawing Sheets

QUANTITATIVE SENSOR AND MANUFACTURING METHOD THEREOF

BACKGROUND OF THE INVENTION

1. Field of the Invention

The present invention relates to a quantitative sensor and the manufacturing method thereof and, more particularly, to a quantitative sensor with high sensitivity and made of dual-mode film bulk acoustic resonator (FBAR).

2. Description of the Related Art

With the development in semi-conductor technology, sensing elements are improved from surface acoustic wave resonators (SAWR) to film bulk acoustic resonators (FBAR). Furthermore, a dual-mode film bulk acoustic resonator is mainly composed of two electrodes and a piezoelectric layer, which has a higher quality factor and lower loss in energy since the resonant waves are transmitted through solid parts of the dual-mode film bulk acoustic resonator, wherein a bulk process is a conventional process for manufacture of the dual-mode film bulk acoustic resonator. The bulk process may etch a rear side of a substrate of a film bulk acoustic resonator to form a structural layer, which may utilize the air nearby to serve as a reflecting layer so as to decrease loss in energy.

Furthermore, in environmental, pharmaceutical and medical fields, a sensor capable of simple operation, fast analysis, and accurate result, especially which can be applied to continuous and real time monitor for various species and samples, is always a desirable invention.

However, conventional film bulk acoustic resonators cannot be used to sense targets such as liquid or bio-samples, and thus the film bulk acoustic resonators have not been utilized to form a fluid sensor or a biosensor with high sensitivity. Therefore, it is necessary to improve the conventional film bulk acoustic resonators to provide a sensor with high sensitivity, accuracy and efficiency.

SUMMARY OF THE INVENTION

It is therefore the primary objective of this invention to provide a quantitative sensor and manufacturing method thereof, with the quantitative sensor including a dual-mode FBAR capable of providing high accuracy, sensitivity and efficiency in quantitative detection.

The invention discloses a quantitative sensor including a substrate, a first electrode layer, a piezoelectric layer, a second electrode layer, a binding metal layer and a fluid detection metal layer. The substrate has a chamber linking two opposite sides of the substrate, with one of the two opposite sides being a coupling side. The first electrode layer is mounted on the coupling side of the substrate and in communication with the chamber. The piezoelectric layer is mounted on the first electrode layer and has a growing direction, wherein there is an angle between a surface of the coupling side and the said growing direction, and the angle is less than 90 degrees but larger than 0 degree. The second electrode layer is formed on the piezoelectric layer and separated from the first electrode layer. The binding metal layer is received in the chamber and mounted on the first electrode layer. The fluid detection metal layer is also received in the chamber but mounted on the binding metal layer.

The invention also discloses a quantitative sensor including a substrate, a first electrode layer, a piezoelectric layer, a second electrode layer, a binding metal layer, a biocompatible metal layer and a bio-sensing layer. The substrate has a chamber linking two opposite sides of the substrate, with one of the two opposite sides being a coupling side. The first electrode layer is mounted on the coupling side of the substrate and in communication with the chamber. The piezoelectric layer is mounted on the first electrode layer and has a growing direction, wherein there is an angle between a surface of the coupling side and the said growing direction, and the angle is less than 90 degrees but larger than 0 degree. The second electrode layer is formed on the piezoelectric layer and separated from the first electrode layer. The binding metal layer is received in the chamber and mounted on the first electrode layer. The biocompatible metal layer is received in the chamber and mounted on the binding metal layer. The bio-sensing layer is received in the chamber and mounted on the biocompatible metal layer.

The invention further discloses that, for both of the above said quantitative sensors, the angle between the surface of the coupling side and the said growing direction is 75-45 degrees.

The invention also discloses a manufacturing method of quantitative sensor, which comprises: forming a first electrode layer on a coupling side of a substrate; etching the substrate from a side opposite to the coupling side toward the coupling side to form a chamber communicating with the first electrode layer; forming a piezoelectric layer on the first electrode layer with a growing direction, wherein there is an angle between a surface of the coupling side and the said growing direction, and the angle is 75-45 degrees; forming a second electrode layer on the piezoelectric layer and separated from the first electrode layer; forming a binding metal layer in the chamber on the first electrode layer; and forming a fluid detection metal layer in the chamber on the binding metal layer.

The invention further discloses that a plasma clean process is performed to clean a surface of the fluid detection metal layer that exposed to the chamber after the fluid detection metal layer is formed.

The invention also discloses a manufacturing method of quantitative sensor, which comprises: forming a first electrode layer on a coupling side of a substrate; etching the substrate from a side opposite to the coupling side toward the coupling side to form a chamber communicating with the first electrode layer; forming a piezoelectric layer on the first electrode layer with a growing direction, wherein there is an angle between a surface of the coupling side and the said growing direction, and the angle is 75-45 degrees; forming a second electrode layer on the piezoelectric layer and separated from the first electrode layer; forming a binding metal layer in the chamber on the first electrode layer; forming a biocompatible metal layer in the chamber on the binding metal layer; and forming a bio-sensing layer in the chamber on the biocompatible metal layer.

The invention further discloses that the bio-sensing layer is formed by pouring a cysteine solution into the chamber and keeping it still for a predetermined time period after the biocompatible metal layer to from a cysteine layer as the bio-sensing layer.

The invention further discloses that the bio-sensing layer is cleaned by deionized water.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
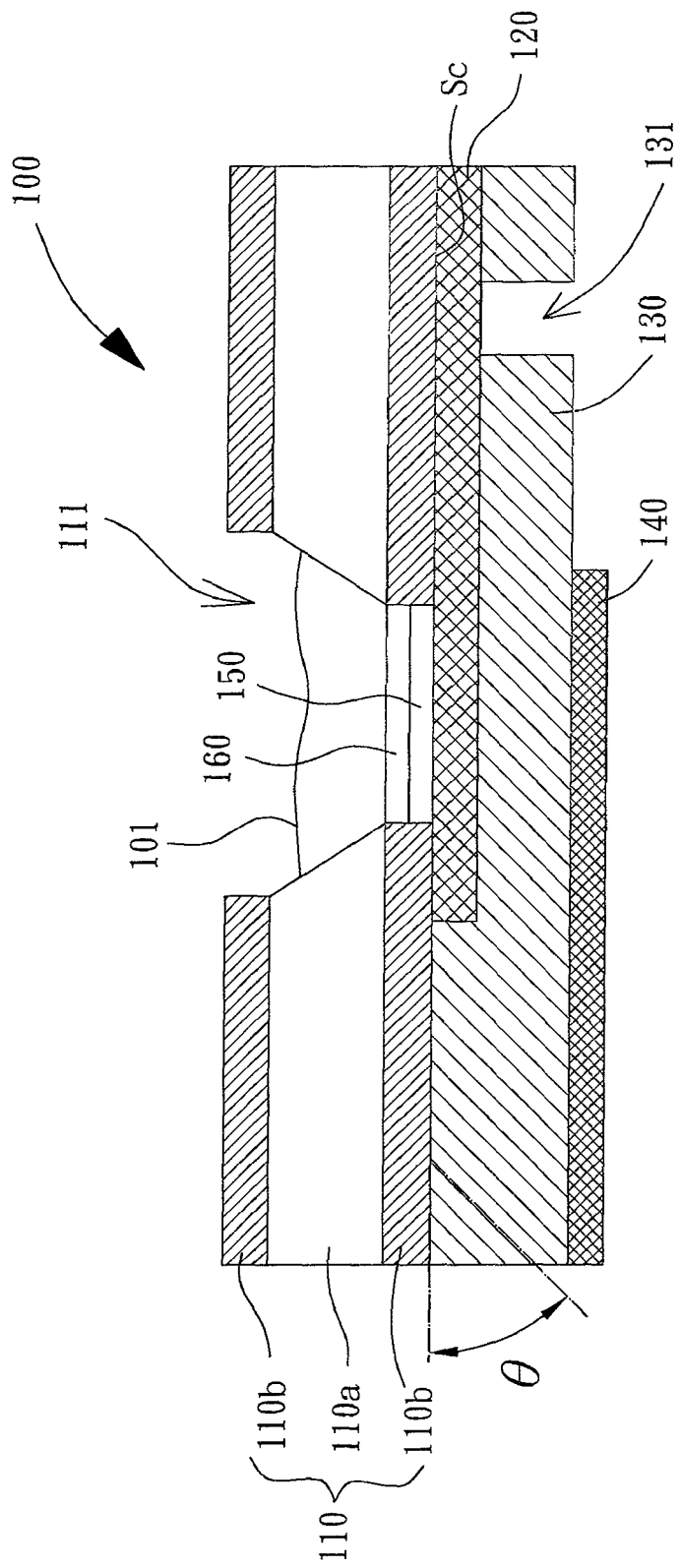
FIG. 1 shows a cross-sectional view of a quantitative sensor according to a first embodiment of the invention.

In the various figures of the drawings, the same numerals designate the same or similar parts. Furthermore, when the term "first," "second," "upper," "lower," and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Please refer to FIG. 1. A cross-sectional view of a quantitative sensor according to a first embodiment of this invention is shown. The shown quantitative sensor is a fluid sensor 100 for detecting a liquid sample 101 such as sulfuric acid liquid. The fluid sensor 100 includes a substrate 110, a first electrode layer 120, a piezoelectric layer 130, a second electrode layer 140, a binding metal layer 150, and a fluid detection metal layer 160.

The substrate 110 has a chamber 111 linking two opposite sides of the substrate 110 and adapted to receive the liquid sample 101. The first electrode layer 120, piezoelectric layer 130 and second electrode layer 140 are sequentially arranged on one of the two opposite sides of the substrate 110 in order, with the said side being defined as a coupling side "Sc" in the following content, while the binding metal layer 150 and fluid detection metal layer 160 are formed inside the chamber 111. The first electrode layer 120 is arranged on the coupling side "Sc" and communicates with the chamber 111. The piezoelectric layer 130 partially covers but reveals the first electrode layer 120. The second electrode layer 140 is formed on the piezoelectric layer 130 and separated from the first electrode layer 120 via the piezoelectric layer 130. The binding metal layer 150 is formed in the chamber 111 on the first electrode layer 120. The fluid detection metal layer 160 is also formed in the chamber 111, with the fluid detection metal layer 160 mounted on the binding metal layer 150.

Preferably, the substrate 110 includes a body 110a and two protection layers 110b, with the body 110a being a silicon substrate, and with the two protection layers 110b respectively forming the said two opposite sides of the body 110a and being made of silicon nitride (SiNx) to protect and to support the body 110a. The first electrode layer 120 can be made of metal such as aluminum (Al), gold (Au), molybdenum (Mo), or platinum (Pt), and the first electrode layer 120 is preferably made of platinum in this embodiment. The piezoelectric layer 130 is made of piezoelectric material such as aluminum nitride, zinc oxide or selenium sulfide, and the piezoelectric layer 130 is made of zinc oxide in this embodiment. Particularly, a growing direction of grains of a zinc oxide film serving as the piezoelectric layer 130 is inclined relative to a c-axis of the coupling side "Sc." Namely, there is an angle "θ" between the surface of the coupling side "Sc" and the said growing direction, wherein the angle "θ" is less than 90 degrees but larger than 0 degree, and preferable between 75-45 degrees for a desirable performance. With the said angle "θ," the frequency of a shear resonance wave can be obviously observed, and thus the provided quantitative sensor is capable of detecting the weight or concentration of the liquid sample 101 received in the chamber 111.

The material of the second electrode layer 140 may also be selected from one of aluminum (Al), gold (Au), molybdenum (Mo) and platinum (Pt), and the second electrode layer 140 is made of molybdenum in this embodiment. The binding metal layer 150 is mounted on a part of the first electrode layer 120 that is exposed to the chamber 111, and the binding metal layer 150 is adapted to enhance the combination between the first electrode layer 120 and the fluid detection metal layer 160, so that the fluid detection metal layer 160 can be firmly fixed above the first electrode layer 120 via the binding metal layer 150. In this embodiment, the binding metal layer 150 is made of chromium (Cr). The fluid detection metal layer 160 is made of metal with high hydrophile property such as gold (Au), preferably nano-Au, or nickel (Ni) so as to sense the liquid sample 101 and to accurately respond to the character of the liquid sample 101 by a resonance wave transmitted by the first electrode layer 120, and the material of the fluid detection metal layer 160 is gold in this embodiment. As a result, the fluid detection metal layer 160 in the chamber 111 may hydrophilically contact with the liquid sample 101 when the chamber 111 receives the liquid sample 101 and thus the accuracy of the detected result can be improved.

Figure 2A:
FIGS. 2A-2I show cross-sectional views of semi-finished materials of the quantitative sensor during manufacture thereof.
Figure 2B:
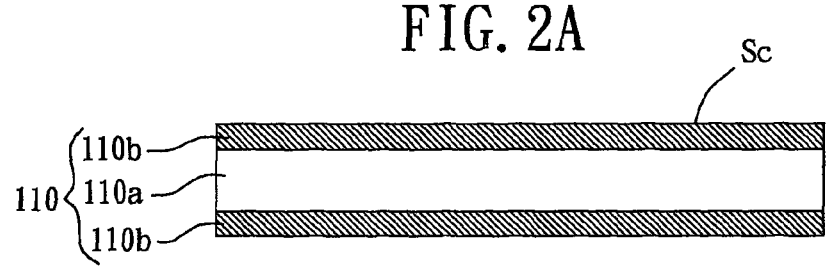
Figure 2C:
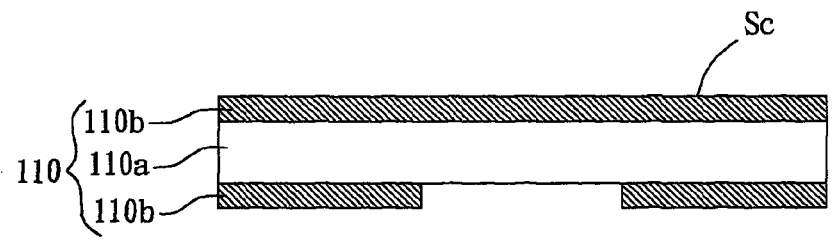
Figure 2D:
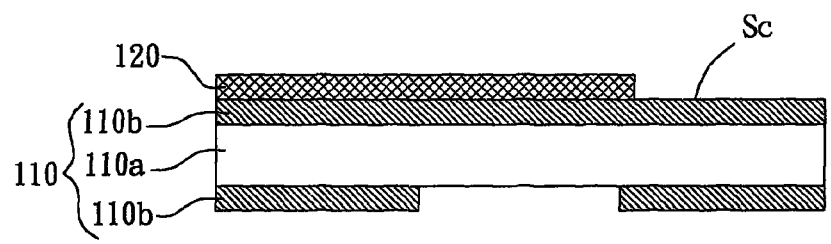
Figure 2E:
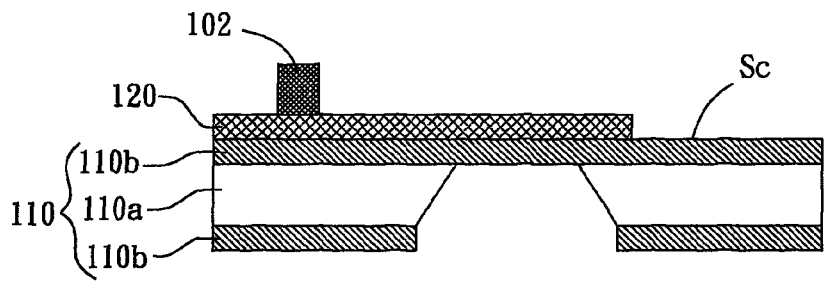

Regarding to the manufacturing method of the quantitative sensor of this embodiment, please refer to FIGS. 2A-2I. Referring to FIG. 2A, the body 110a of the substrate 110 is previously provided, and it is preferable that the body 110a is processed through a cleaning step to have cleaned surfaces. Referring to FIG. 2B, the two protection layers 110b are respectively formed on the two opposite sides of the body 110a, wherein the protection layers 110b are preferably formed through "low pressure chemical vapor deposition (LPCVD)" so as to form silicon nitride layers serving as the protection layers 110b. Referring to FIG. 2C, the substrate 110 is etched from one side thereof toward the other side of the substrate 110 for removing a part of one of the protection layers 110b in a predetermined area, with the predetermined area designed to form the chamber 111 and the un-etched side serving as the coupling side "Sc". Preferably, the etching process performed onto the protection layer 110b of the substrate 110 is the reactive ion etching (RIE) process of conventional dry etching processes. Referring to FIG. 2D, the first electrode layer 120 is formed on the coupling side "Sc" of the substrate 110, wherein a part of the coupling side "Sc" is uncovered by the first electrode layer 120, with the first electrode layer 120 totally covering an area of the coupling side "Sc" opposite to the said predetermined area. Besides, the way to form the first electrode layer 120 on the protection layer 110b can be the conventional direct current (DC) sputter. Referring to FIG. 2E, the substrate 110 is further etched from the etched protection layer 110b into the body 110a, so as to remove a part of the body 110a adjacent to the predetermined area till the un-etched protection layer 110b is shown. The etching process performed onto the body 110a of the substrate 110 can be selected from one of conventional wet and dry etching processes. Besides, a thick photo-resisting layer 102 is also formed on the first electrode layer 120.

Figure 2F:
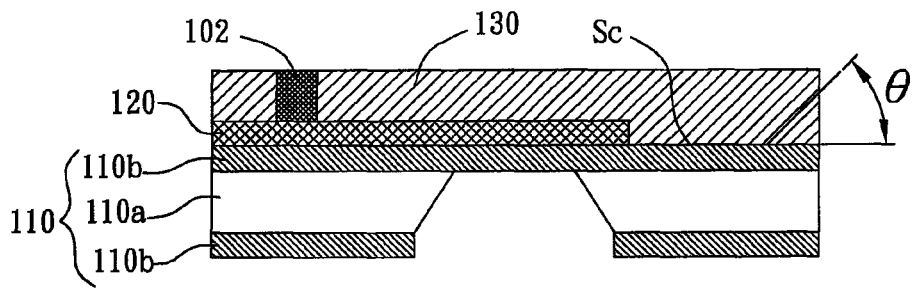
Figure 2G:
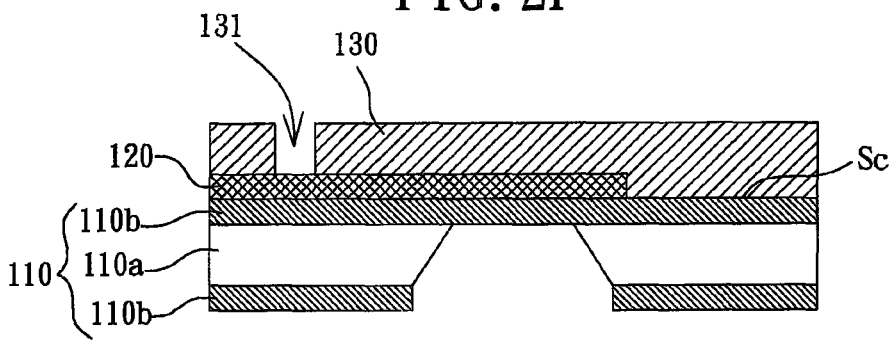
Figure 2H:
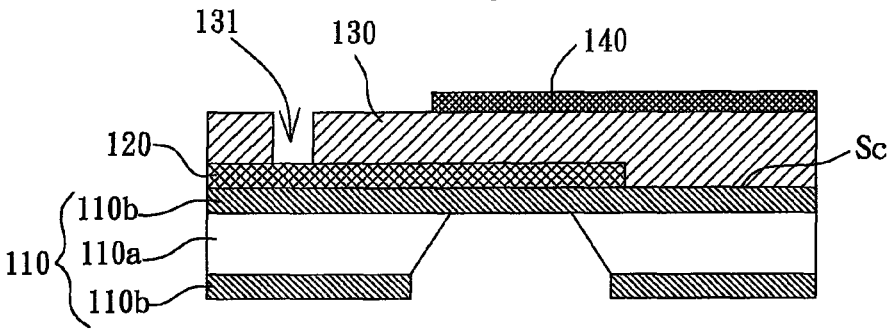
Figure 2I:
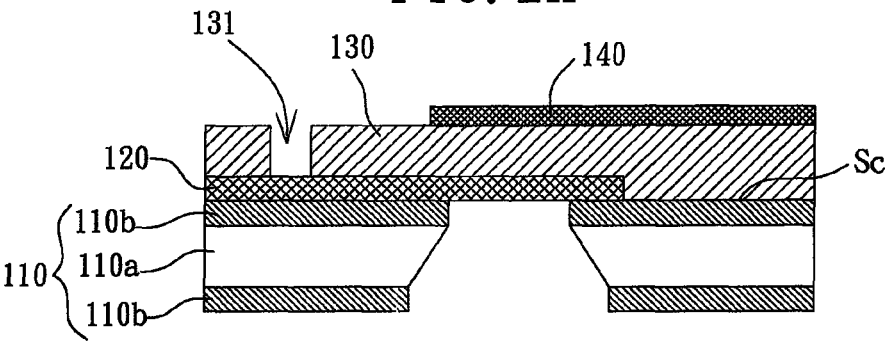

Referring to FIG. 2F, the piezoelectric layer 130 is then formed on the first electrode layer 120 and the coupling side "Sc" by radio frequency (RF) sputter, with the piezoelectric layer 130 surrounding the photo-resisting layer 102. Referring to FIG. 2G the photo-resisting layer 102 is removed to reveal a channel 131 in the piezoelectric layer 130 and in communication with the first electrode layer 120. Referring, to FIG. 2H, the second electrode layer 140 is formed on the piezoelectric layer 130 by DC sputter and does not cover the channel 131. Referring to FIG. 2I, a part of the protection layer 110b between the body 110a and the first electrode layer 120, which is corresponding to the said predetermined area, is etched so as to form the whole chamber 111 in the substrate 110 and to reveal the first electrode layer 120 to the chamber 111. Finally, the binding metal layer 150 and the fluid detection metal layer 160 are respectively and sequentially formed in the chamber 111 above the first electrode layer 120, so that the quantitative sensor with a dual-mode film bulk acoustic resonator structure of the first embodiment of the present invention is thus completed. Preferably, in order to improve the hydrophile property of the fluid detection metal layer 160, it is preferable to perform a plasma clean process, such as oxygen plasma clean process, for the surface of the fluid detection metal layer 160 that exposed to the chamber 111.

Specifically, when the quantitative sensor is in use, the first electrode layer 120 is adapted to electrically connect with a first wire passing through the channel 131, the second electrode layer 140 is adapted to electrically connect with a second wire, and one of the first and second wires connects to a resonator circuit while the other one of the first and second wires connects to an oscilloscope. Accordingly, the oscilloscope may show a frequency response of a signal sent by the resonator circuit and passing through the present quantitative sensor.

Figure 3:
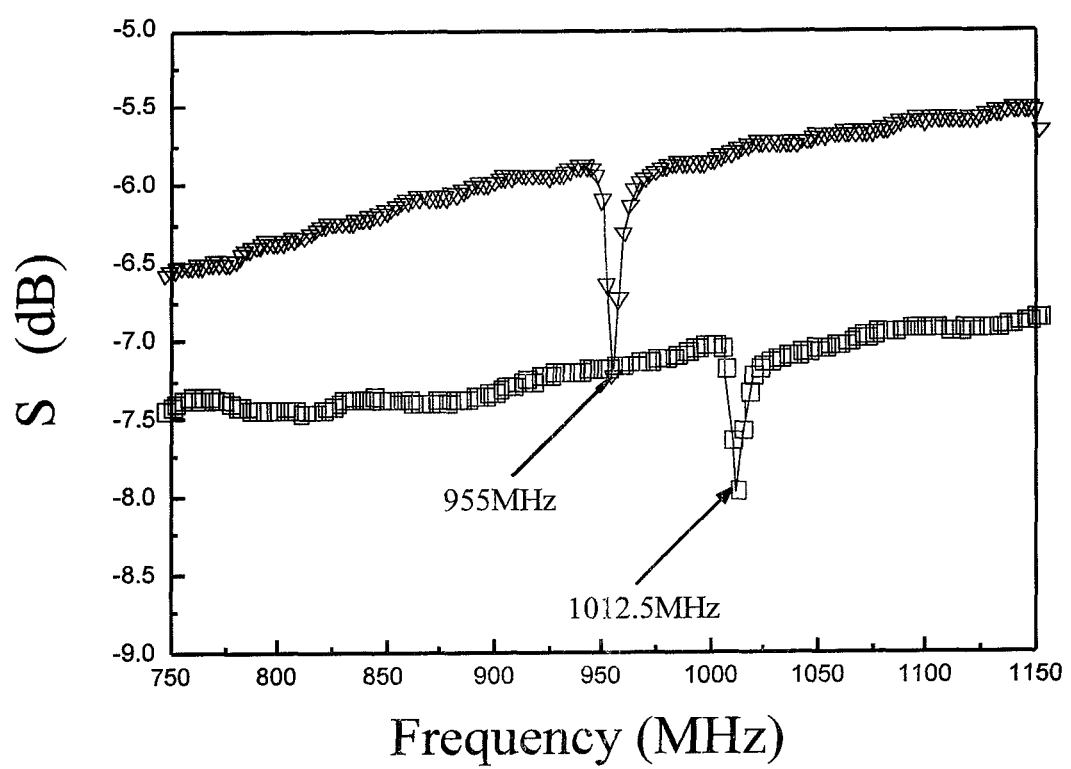
FIG. 3 shows Bode plots of responses of signals passing through the quantitative sensor.

Please refer to FIG. 3, which are Bode plots of frequency responses of the said signal, with the upper line showing the Bode plot of the signal when the chamber 111 is empty, and with the lower line showing the Bode plot of the signal when the chamber 111 receives a liquid sample 101. Specifically, about the upper and lower lines in FIG. 3, a sharp trough at a first shear frequency "fs1" of 955 MHZ of the upper line is shown, and the sharp trough shifts towards a second shear frequency "fs2" of 1012.5 MHz of the lower line when the liquid sample 101 is poured into the chamber 111. Particularly, the scale of the sharp trough is large when the angle "θ" between the surface of the coupling side "Sc" and the said growing direction of the piezoelectric layer 130 is arranged between 75-45 degrees. The above phenomenon is caused by the changes in the electric conductivity of the piezoelectric layer 130, which is due to the added liquid sample 101, and the change in velocity of the surface acoustic wave of the piezoelectric layer 130. Finally, with the change in velocity of the surface acoustic wave of the piezoelectric layer 130, the sharp trough is shifted, wherein the change in velocity may be affected by physical characters of the liquid sample 101, such as weight, viscosity, and conductivity thereof. Furthermore, a relationship between the change in velocity and the conductivity can be shown as the following equation (1):

$$\frac{\Delta v}{v_0} = \frac{k^2}{2} \cdot \frac{1}{1+(\sigma/\sigma_m)}, \quad (1)$$

wherein the Δv denotes the change in velocity, the $v_0$ denotes an original velocity of the surface acoustic wave of the piezoelectric layer 130 when the chamber 111 is empty, the $k^2$ denotes a constant due to chemical-electrical coupling, the σ denotes the conductivity when the chamber 111 is empty, and the $\sigma_m$ denotes the conductivity when the chamber 111 receives the liquid sample 101.

Figure 4:
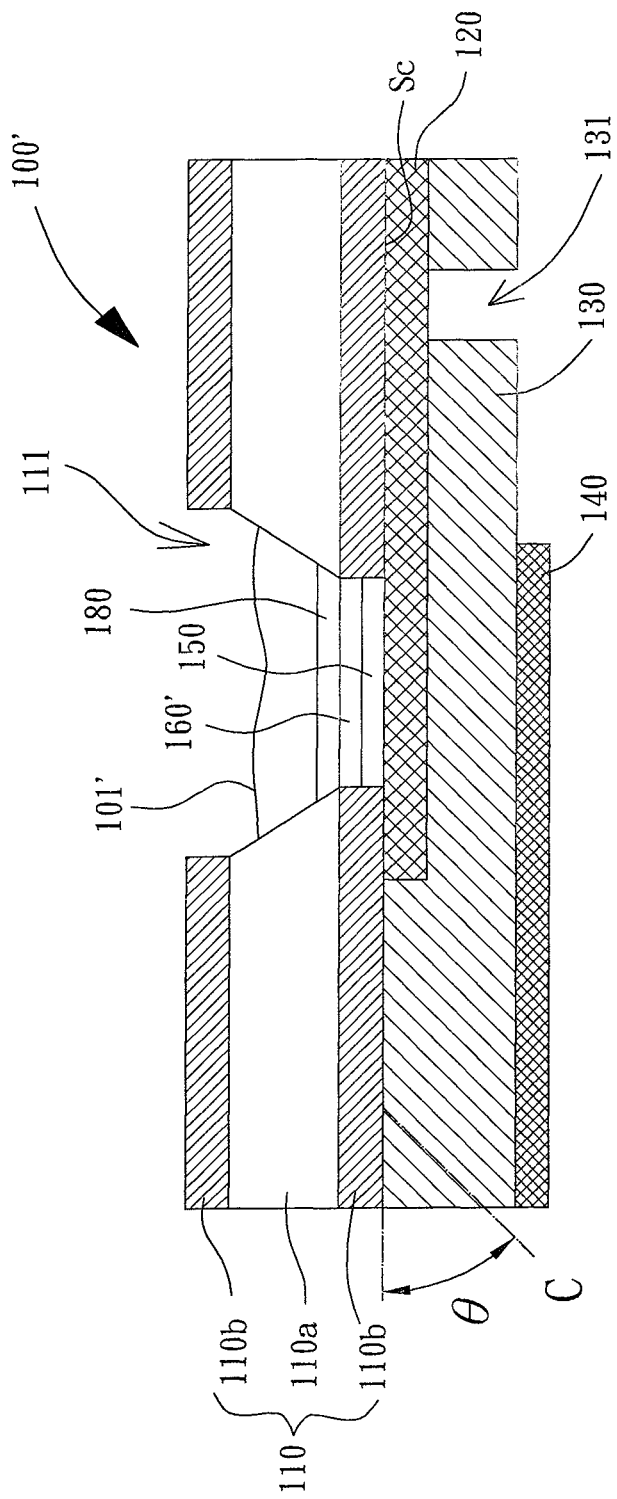
FIG. 4 shows a cross-sectional view of another quantitative sensor according to a second embodiment of the invention.

Now, please refer to FIG. 4, which shows a cross-sectional view of a quantitative sensor according to a second embodiment of this invention. In comparison with the fluid sensor 100 of the first embodiment, the quantitative sensor is a biosensor 100' for detecting a bio-sample 101', and the difference between these two embodiments lies in that, instead of the fluid detection metal layer 160 of the first embodiment, the biosensor 100' has a biocompatible metal layer 160' and a bio-sensing layer 180. Specifically, the biocompatible metal layer 160' is made of a metal having high biocompatibility, such as gold, and this biocompatible metal layer 160' is mounted on the binding metal layer 150 and adapted to connect with and fix the bio-sensing layer 180 in the chamber 111. The bio-sensing layer 180 is arranged for first affinity bio-molecules to be coated thereon, so that the quantity of second affinity bio-molecules in the bio-sample 101' can be measured after the bio-sample 101' is poured into the chamber 111 and the second affinity bio-molecules bind to the first affinity bio-molecules specifically. Furthermore, the method to form the bio-sensing layer 180 includes: pouring a cysteine solution into the chamber 111 and keeping it still for a predetermined time period, such as 1 hour, after the biocompatible metal layer 160' is formed, so as to from a cysteine layer serving as the bio-sensing layer 180; and cleaning the cysteine layer by deionized (ID) water.

Particularly, in accordance with the second affinity bio-molecules, the first affinity bio-molecules are selected from a kind of bio-molecules such as antigen, antibody, nucleic acid, enzyme, protein etc. that can specifically bind to antibody, antigen, nucleic acid, enzyme, microorganism etc. serving as the second affinity bio-molecule. Accordingly, when the first and second affinity bio-molecules bind to each other, the weight of the second affinity bio-molecules will change the electric conductivity and velocity of the surface acoustic wave of the piezoelectric layer 130, and therefore the weight of the second affinity bio-molecules in the bio-sample 101' can be shown by the change in the shear frequency and thus be measured. As a result, the biosensor 100' of this embodiment may provide a detecting result in a short time period since the binding reaction between the first and second affinity bio-molecules is fast, so that the convenience and efficiency in bio-detection can be largely enhanced.

In sum, the provided quantitative sensor of the embodiments of the invention not only successfully applies the FBAR technique to detection of liquid and bio-samples, but also largely improves the accuracy, sensitivity, and efficiency of quantitative detection in environmental, pharmaceutical and medical fields by the characters of a FBAR.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A quantitative sensor, comprising:
    a substrate having a chamber linking two opposite sides of the substrate, with one of the two opposite sides being a coupling side, wherein the chamber is adapted to be filled with liquid to be detected;
    a first electrode layer mounted on the coupling side of the substrate and in communication with the chamber;
    a piezoelectric layer mounted on the first electrode layer and having a growing direction, wherein there is an angle between a surface of the coupling side and the said growing direction, and the angle is 75-45 degrees;
    a second electrode layer formed on the piezoelectric layer and separated from the first electrode layer;
    a binding metal layer disposed in the chamber and mounted on the first electrode layer; and
    a fluid detection metal layer disposed in the chamber and mounted on the binding metal layer.

2. The quantitative sensor as claimed in claim 1, wherein the binding metal layer is made of chromium.

3. The quantitative sensor as claimed in claim 1, wherein the fluid detection metal layer is made of gold.

4. The quantitative sensor as claimed in claim 1, wherein the piezoelectric layer is made of zinc oxide.

5. A method of manufacturing a quantitative sensor, comprising:
   forming a first electrode layer on a coupling side of a substrate;
   etching the substrate from a side opposite to the coupling side toward the coupling side to form a chamber communicating with the first electrode layer;
   forming a piezoelectric layer on the first electrode layer with a growing direction, wherein there is an angle between a surface of the coupling side and the said growing direction, and the angle is 75-45 degrees;
   forming a second electrode layer on the piezoelectric layer and separated from the first electrode layer;
   forming a binding metal layer in the chamber on the first electrode layer; and
   forming a fluid detection metal layer in the chamber on the binding metal layer.

6. The method of manufacturing a quantitative sensor as claimed in claim 5, wherein a plasma cleaning process is performed to clean a surface of the fluid detection metal layer that is exposed to the chamber after the fluid detection metal layer is formed.

7. A quantitative sensor, comprising:
   a substrate having a chamber linking two opposite sides of the substrate, with one of the two opposite sides being a coupling side, wherein the chamber is adapted to be filled with liquid to be detected;
   a first electrode layer mounted on the coupling side of the substrate and in communication with the chamber;
   a piezoelectric layer mounted on the first electrode layer and having a growing direction, wherein there is an angle between a surface of the coupling side and the said growing direction, and the angle is 75-45 degrees;
   a second electrode layer formed on the piezoelectric layer and separated from the first electrode layer;
   a binding metal layer disposed in the chamber and mounted on the first electrode layer;
   a biocompatible metal layer disposed in the chamber and mounted on the binding metal layer;
   a bio-sensing layer disposed in the chamber and mounted on the biocompatible metal layer.

8. The quantitative sensor as claimed in claim 7, wherein the binding metal layer is made of chromium.

9. The quantitative sensor as claimed in claim 7, wherein the biocompatible metal layer is made of gold.

10. The quantitative sensor as claimed in claim 7, wherein the bio-sensing layer is made of cysteine.

11. The quantitative sensor as claimed in claim 7, wherein the piezoelectric layer is made of zinc oxide.

12. A method of manufacturing a quantitative sensor, comprising:
    forming a first electrode layer on a coupling side of a substrate;
    etching the substrate from a side opposite to the coupling side toward the coupling side to form a chamber communicating with the first electrode layer;
    forming a piezoelectric layer on the first electrode layer with a growing direction, wherein there is an angle between a surface of the coupling side and the said growing direction, and the angle is 75-45 degrees;
    forming a second electrode layer on the piezoelectric layer and separated from the first electrode layer;
    forming a binding metal layer in the chamber on the first electrode layer;
    forming a biocompatible metal layer in the chamber on the binding metal layer; and
    forming a bio-sensing layer in the chamber on the biocompatible metal layer.

13. The method of manufacturing a quantitative sensor as claimed in claim 12, wherein the bio-sensing layer is formed by pouring a cysteine solution into the chamber and keeping it still for a predetermined time period after the biocompatible metal layer to from a cysteine layer as the bio-sensing layer.

14. The method of manufacturing a quantitative sensor as claimed in claim 13, wherein the bio-sensing layer is cleaned by deionized water.

* * * * *